United States Patent [19]

Podszun et al.

[11] Patent Number: 5,621,119
[45] Date of Patent: Apr. 15, 1997

[54] DI(METH)ACRYLATES HAVING CYCLIC CARBONATE GROUPS

[75] Inventors: Wolfgang Podszun, Köln; Klaus Schäpers, Pulheim; Werner Finger, Neuss; Ludger Heiliger, Leverkusen; Carl Casser, Köln, all of Germany

[73] Assignee: Heraeus Kulzer GmbH & Co., KG, Hanau, Germany

[21] Appl. No.: 502,340

[22] Filed: Jul. 14, 1995

[30] Foreign Application Priority Data

Jul. 22, 1994 [DE] Germany ............... 44 26 129.2

[51] Int. Cl.$^6$ ............ C07D 317/36; A61C 13/23
[52] U.S. Cl. ............ 549/229; 433/226; 433/228.1
[58] Field of Search ............ 549/229; 433/226, 433/228.1

[56] References Cited

U.S. PATENT DOCUMENTS

| | | | |
|---|---|---|---|
| 2,446,145 | 7/1948 | Strain | 260/338 |
| 3,774,305 | 11/1973 | Stoffey et al. | 32/15 |
| 4,017,454 | 4/1977 | Muller | 260/42.52 |
| 4,323,348 | 4/1982 | Schmitz-Josten et al. | 433/228 |
| 4,323,696 | 4/1982 | Schmitz-Josten et al. | 560/220 |
| 5,122,061 | 6/1992 | Wakumoto et al. | 433/228.1 |
| 5,132,458 | 7/1992 | Honel et al. | 564/367 |
| 5,466,811 | 11/1995 | Alexander | 546/283 |
| 5,486,548 | 1/1996 | Podszun et al. | 523/115 |

FOREIGN PATENT DOCUMENTS

| | | |
|---|---|---|
| 1155131 | 10/1983 | Canada. |
| 0406057 | 6/1989 | European Pat. Off. |
| 3135115 | 3/1983 | Germany. |

OTHER PUBLICATIONS

T. Fukushima et al, Dental Materials Journal, vol, 4, No. 1, pp. 33–39 (1985).
D. Gachter et al, Taschenbach der Kunststaff–Additive, 3rd ed., Carl Hanser Verlag, Munchen (1992).
W. Finger et al., Zahlheilkunde, vol. 86, pp. 812–824, (1976).
Ollmann Encyclopadie der technischen Chemie, 4 Auflage, vol. 8, pp. 19–45, Verlog Chemie.
G.M. Brauer et al., Am. Chem. Soc. Symp. Ser. 212, pp. 359–371, (1983).

Primary Examiner—Mukund J. Shah
Assistant Examiner—Deepak R. Rao
Attorney, Agent, or Firm—Sprung Horn Kramer & Woods

[57] ABSTRACT

The invention relates to diacrylates and dimethacrylates having cyclic carbonate groups, and their use in dental materials.

7 Claims, No Drawings

DI(METH)ACRYLATES HAVING CYCLIC CARBONATE GROUPS

The invention relates to diacrylates and dimethacrylates having cyclic carbonate groups, and their use in dental materials.

Di(meth)acrylates are used in the dental sector, for example as a component of plastics filling materials, dental coatings, sealants, fastening materials and facing materials.

A particularly frequently used monomer is so-called bisGMA of the formula (I)

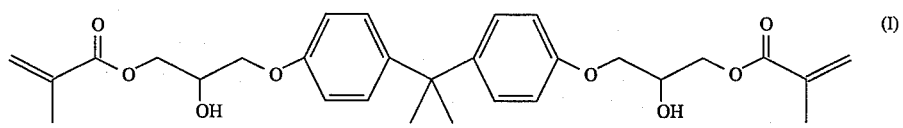

Materials obtained from bisGMA have an advantageous level of mechanical properties. A preferred hardening method for many applications is photopolymerization with exposure to visible light. For the hardening of dental filling materials, the required exposure time is usually 15 to 60 s. The depths of hardening are in general a few mm and are substantially lower in the case of highly pigmented filling materials than in the case of transparent filling materials. In the case of deep cavities, the dentist must harden the filling layer by layer.

A deficiency of all photopolymerizable dental materials known to date is that they do not harden at the free surface in contact with atmospheric oxygen. This phenomenon known as polymerization inhibition requires particular measures for the exclusion of atmospheric oxygen. A highly effective measure in the case of smooth surfaces is covering with a transparent oxygen-impermeable film. For geometrically complicated surfaces, protective matings (for example of polyvinyl alcohol) which are applied from solution were proposed as an oxygen barrier, but this method is not only expensive but also fairly ineffective. In many cases, the dentist resorts to using an excess of dental material and removing the unpolymerized part after exposure in a subsequent processing step. This method too has serious disadvantages: the surface geometry can be produced only in a very inexact manner. The boundary between unpolymerized or insufficiently polymerized material on the one hand and completely hardened material on the other hand is not detectable, so that there is a danger that a surface which is not optimally hardened will be obtained on subsequent processing.

The object of the present invention is to provide novel monomers having a higher polymerization rate and less sensitivity to polymerization inhibition by oxygen, in particular for applications in the dental sector.

The object is achieved, according to the invention, by monomers having cyclic carbonate groups according to the formula (II)

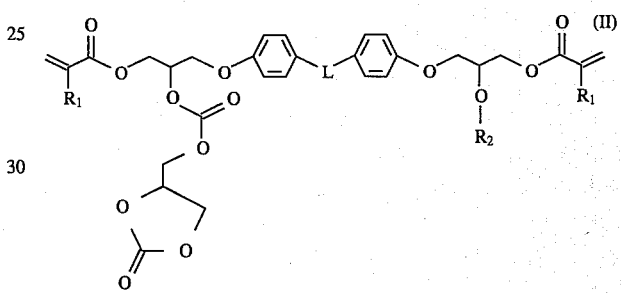

wherein $R_1$ independently of one mother represent hydrogen or methyl, $R_2$ represents hydrogen or

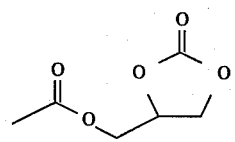

and

L represents a direct C—C bond, —O—, —S—, —SO$_2$— —CO— or a $C_1$- to $C_{15}$-alkylene radical which my be substituted by alkyl, hydroxyl or halogen or a cyclohexylidene radical which may be substituted by methyl up to 3 times.

Preferred examples of L are mentioned below:

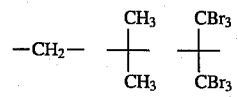

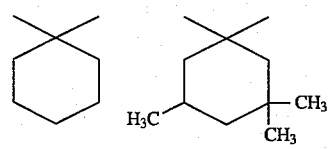

TABLE 1
Monomers according to the invention
Monomer 1
Monomer 2
Monomer 3
Monomer 4
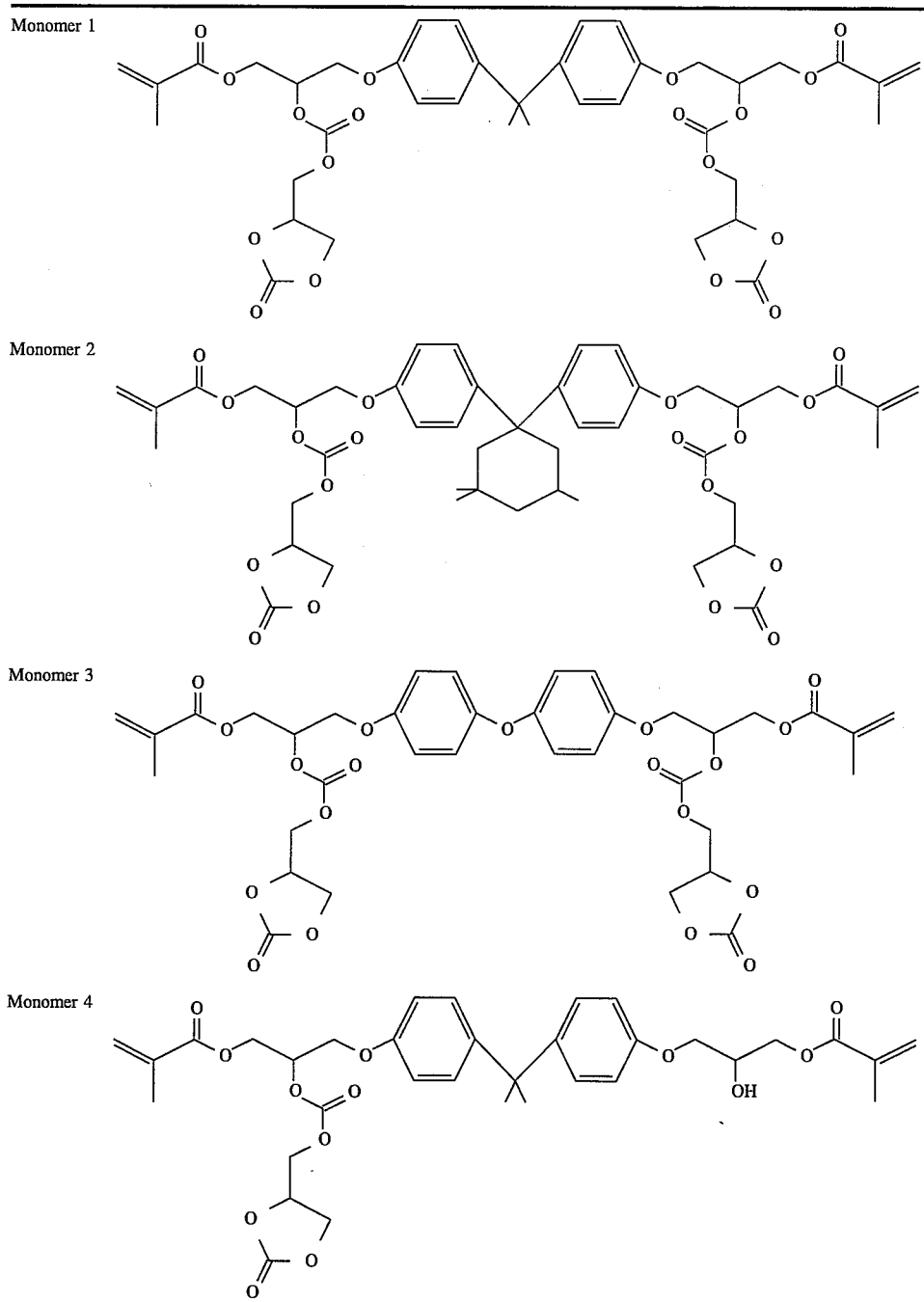

TABLE 1-continued

Monomers according to the invention

Monomer 5

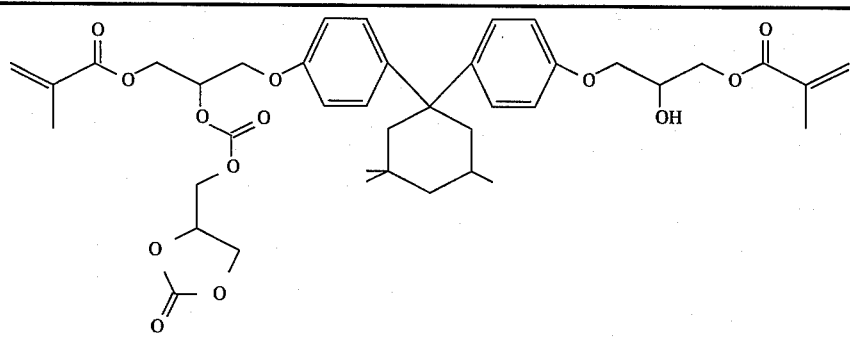

The synthesis of the (meth)acrylates according to the invention and having cyclic carbonate groups is carried out in an advantageous manner by reacting the parent hydroxy compound with the chloroformic acid ester according to the formula (III).

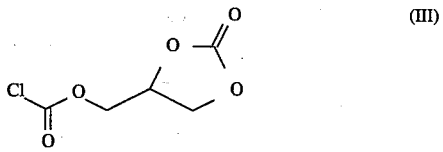 (III)

The chloroformic acid ester according to the formula (III) can be prepared by phosgenation of glycerol. This synthesis step is described in detail in U.S. Pat. No. 2,446,145.

For the use of the monomers according to the invention in polymerizable dental restoration materials, the (meth)acrylic acid esters according to the invention can be mixed with monomers known per se. For example, bisGMA of the formula (I) and urethane methacrylates which are obtainable by reacting diisocyanates with hydroxyethyl methacrylate are particularly suitable components of the mixture.

The viscosity of the monomers according to the invention is lower than that of the conventional compounds (for example bisGMA), so that compounds of the formula (II), according to the invention, can also be used undiluted, that is to say in pure form. If an even lower viscosity is desired, comonomers of low viscosity can be mixed with the monomers according to the invention, as reactive diluents or solvents. The compounds according to the invention are then used as a mixture with comonomers in an mount of not less than 10% by weight, preferably 20% by weight.

The following comonomers may be mentioned by way of example: glyceryl dimethacrylate, triethylene glycol dimethacrylate (TEGDMA), tetraethylene glycol dimethacrylate, 1,12-dodecanediol dimethacrylate, 1,6-hexanediol dimethacrylate, diethylene glycol dimethacrylate, 2,2-bis-[p-(2'-hydroxy-3'-methacryloyloxypropoxy)-phenyl]-propane, 2,2-bis-[p-(2'-methacryloyloxyethoxy)phenyl]-propane, trimethylol-propane tri(meth)acrylate, bis-(meth)acryloyloxyethoxymethyl-tricyclo[5.2.1.0$^{2.6}$]-decane (DE-A-29 31 925 and DE-A-29 31 926).

Comonomers which have a boiling point above 100° C. at 13 mbar are particularly preferred.

The (meth)acrylic acid esters according to the invention, optionally as a mixture with the stated comonomers, can be hardened by methods known per se to give crosslinked polymers (Am. Chem. Soc. Symp. Ser. 212, 359–371 (1983)). A system comprising a peroxide compound and a reducing agent, for example based on tertiary aromatic amines, is suitable for the so-called redox polymerization. Examples of peroxides are: dibenzoyl peroxide, dilauroyl peroxide and di-4-chlorobenzoyl peroxide.

N,N-Dimethyl-p-toluidine, bis-(2-hydroxyethyl)-p-toluidine, bis-(2-hydroxyethyl)-3,5-dimethylaniline and N-methyl-N-(2-methylcarbamoyloxypropyl)-3,5-dimethylaniline may be mentioned as examples of tertiary aromatic amines. The concentration of the peroxide and that of the amine are advantageously chosen so that they are 0.1 to 5% by weight, preferably 0.5 to 3% by weight, relative to the monomer mixture.

The peroxide-containing or amine-containing monomer mixtures are stored separately until required for use.

The monomers according to the invention may also be polymerized by exposure to UV light or visible light. Examples of initiators suitable for the photoinitiated polymerization are benzil, benzil dimethyl ketal, benzoin monoalkyl ether, benzophenone, p-methoxybenzophenone, fluorenone, thioxanthone, phenanthroquinone and 2,3-bornanedione (campherquinone), optionally in the presence of activators having a synergistic effect, such as N,N-dimethylaminoethyl methacrylate, triethanolamine or 4-N,N-dimethylaminobenzenesulphonic acid diallylamide. The procedure for the photopolymerization is described, for example, in DE-A- 3 135 115.

In addition to the initiators described above, light stabilizers and stabilizers known per se for this purpose may be added to the monomers according to the invention.

Light stabilizers are described, for example, in "Gächter, Müller, Taschenbuch der Kunststoff-Additive [Pocket book of plastics additives], 3rd edition, Carl Hanser Verlag". The following light stabilizers may be mentioned by way of example: Cyasorb UV 9®, Tinuvin P®, Tinuvin 770®, Tinuvin 622® and Tinuvin 765®.

Stabilizers are described, for example, in "Ullmanns Encyclopädie der technischen Chemie [Ullmann's Encyclopaedia of Industrial Chemistry], 4th edition, Volume 8, pages 19–45". The following stabilizers may be mentioned by way of example: 2,6-di-tert-butylphenol, 2,6-di-tert-butyl-4-methylphenol, 2,6-di-octadecyl-4-methylphenol and 1,1'-methylene-bis(2-naphthol).

The light stabilizers and the stabilizers may each be used in an amount of 0.01 to 0.5 part by weight, relative to 100 parts by weight of the monomer mixture.

The monomer mixtures may also be used, with or without the addition of fillers, as coating materials (dental matings) and as adhesives (enamel and dentine).

When used as dental filling materials or fastening materials, fillers are generally added to the monomer mixtures obtained. Monomer mixtures which have a viscosity in the range from 60 to 10,000 mPa·s are particularly advantageous for obtaining a high degree of filling.

Inorganic fillers are preferably mixed with the monomers according to the invention. Quartz, cristobalite, quartz glass, finely divided silica, alumina and glass ceramics, for example zirconium-containing glass ceramics, may be mentioned by way of example. The inorganic fillers are preferably pretreated with an adhesion promoter in order to improve the binding to the polymer matrix of the polymethacrylate. The adhesion promotion can be achieved, for example, by treatment with organosilicon compounds (Progress in Organic Coatings 11, 297–308 (1983)). 3-Methacryloyloxypropyl-trimethoxysilane is preferably used. The fillers for the dental filling materials according to the invention have in general a mean particle diameter of 0.01 to 100 µm, preferably 0.03 to 50 µm, particularly preferably 0.03 to 5 µm. It may also be advantageous to use, alongside one another, several fillers which have a mean particle diameter differing from one to the other and/or a different silane content.

The filler content of the dental filling material and of the fastening material is in general 5 to 85% by weight, preferably 50 to 80% by weight.

For the preparation of the restoration materials, the components are mixed using commercial kneaders.

The amount of (meth)acrylates according to the invention in the restoration materials is in general 5 to 60% by weight, relative to the restoration material.

Dental coatings, adhesives and restoration aerials which contain the monomers according to the invention have an extremely high polymerization rate, the polymerization being only slightly disturbed by atmospheric oxygen. Great depths of hardening are achieved in the photopolymerization.

In principle, two methods are available for testing the sensitivity of monomers according to the invention to polymerization inhibition by atmospheric oxygen:

1. Determination of the layer thickness of unpolymerized resins at the free surface of thin, disc-shaped samples between two glass sheets. On the basis of the different refractive indices of polymerized and unpolymerized resin, a separation line can be detected under the transmitted-light microscope. Further details on this method are described in the literature: Polymerisationsinhibition durch Sauerstoffbei Kompositfullungsmaterialien und Schmelzversieglern [Polymerization inhibition by oxygen in composite filling materials and enamel sealants], W. Finger and K. Dreyer J örgensen, Schweiz. Mschr. Zahnheilkunde [Swiss monthly journal on dentistry], 86, 812–824 (1976).

2. Determination of the unpolymerized layer thickness by measurement of the sample surface before and after dissolution of the monomer layer in a suitable solvent.

The sensitivity to polymerization inhibition was tested using light-activated monomers, such as 1 and 4 from Table 1, in comparison with a conventional dental monomer mixture (bisGMA-TEGDMA 63:38% w/w) by the above-mentioned Method 2 since, in the case of transparent untilled systems, the boundary of the unpolymerized material can be established only in a very inexact manner by Method 1, owing to meniscus formation.

EXAMPLES

Example 1, Preparation of monomer 1 from Table 1

102.52 g of bisGMA (formula (I)), 44.48 g of triethylamine and 0.16 g of 2,6-di-tert-butylcresol (stabilizer) were dissolved in 500 g of chloroform under a nitrogen atmosphere and cooled to 0° C. Thereafter, 72.22 g of chloroformic acid ester of the formula (III), dissolved in 100 g of chloroform, were slowly metered in and the batch was stirred for a further 10 h at room temperature. The precipitate formed was filtered off and the filtrate was poured onto twice the volume of water. The organic phase was separated off, extracted twice by shaking with 0.1N hydrochloric acid and then extracted by shaking with sodium bicarbonate solution, finally washed with water and dried over sodium sulphate. After filtration and evaporation of the solvent, 120.8 g of monomer 1 from Table 1 remain.

IR $[cm^{-1}]$: 1820 (cyclic carbonate); 1760 (carbonate); 1725 (ester); 1645 (methacryloyl).

Example 2, Preparation of monomer 4 from Table 1

The experiment was carried out as described in Example 1, except that 22.24 g of triethylamine and 36.11 g of chloroformic acid ester of the formula (III) were used.

IR $[cm^{-1}]$: 1820 (cyclic carbonate); 1760 (carbonate); 1725 (ester); 1640, 1620 (methacryloyl).

Example 3, Testing of the photoreactivity of the monomers with the aid of photo-DSC The following components were thoroughly mixed:

| | |
|---|---|
| 5.0 g | monomer |
| 100 mg | campherquinone |
| 250 mg | p-dimethylaminobenzenesulphonic acid $N_3N$-diallylamide |

Campherquinone and p-dimethylaminobenzenesulphonic acid N,N-diallylamide form the photoinitiator system.

The examples were exposed to a halogen lamp (75 W) with a protective heat filter in a DSC apparatus (differential scanning calorimetry) at 30° C. The heat flow during exposure was recorded as a function of time. Samples of the same composition without a photoinitiator were used as a reference. During the experiment, flushing was carded out with nitrogen. For evaluation, the value t-max was determined as a measure of the reaction rate. t-max is the time from the beginning of exposure to when the maximum of the reaction is reached (maximum heat flow). The smaller the t-max, the greater the photoreactivity.

| Monomer | t-max [min] |
|---|---|
| from Example 1 | 0.60 |
| from Example 2 | 0.45 |
| bis-GMA-TEGDMA 62:38% w/w (comparison) | 1.70 |

Example 4, Investigation of the sensitivity to polymerization inhibition by atmospheric oxygen To determine the layer thickness of unpolymerized monomer at the free surface (normal ambient atmosphere), cylindrical metal moulds (diameter=5 mm, h=2 mm) were filled with light-activated monomer (activation as in Example 3) and exposed for 20 seconds using a commercial .polymerization trait (Translux CL, Kulzer GmbH) at a distance of about 2 mm. Immediately after the polymerization, the height coordinates (z values) were determined under a reflected-light microscope by the depth-of-focus method using, in each case, 7 measuring points (x, y) defined by the mechanical stage coordinates, along a straight line, with inclusion of reference points, on the free metal surface. To remove the unpolymerized surface layer, the samples were then washed with ethanol using a brush of medium hardness. The mould was then again mounted in the initial position on the mechanical stage of the microscope. After setting at the original x/y coordinates, the z values were again determined. The difference in height values before and after washing with alcohol corresponds to the monomer layer thickness which had remained on the surface owing to the oxygen-inhibition of the polymerization.

The monomer layer thicknesses were determined using five samples and are listed as mean values and standard deviations in the Table below:

| Monomer | Layer thickness of the unpolymerized monomer [μm] |
| --- | --- |
| from Example 1 | 0.3 ± 0.4 |
| from Example 2 | 0.8 ± 0.2 |
| bis-GMA-TEGDMA 62:38% w/w (comparison) | 11.0 ± 1.4 |

After brushing off with ethanol, the comparative samples exhibited pronounced abrasion marks, whereas brush abrasion marks on the samples obtained from the monomers of Examples 1 and 2 were scarcely detectable at 200 times magnification under the reflected-light microscope. This observation also demonstrates better surface polymerization of the samples obtained from the monomers of Examples 1 and 2 in comparison with the reference sample.

We claim:

1. Compounds of the formula (II)

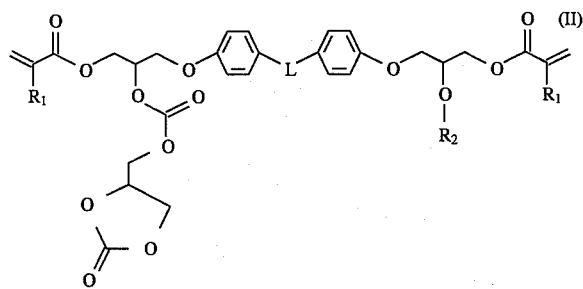

wherein $R_1$ independently of one mother represent hydrogen or methyl, $R_2$ represents hydrogen or

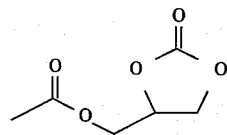

and

L represents a direct C—C bond, —O—, —S—, —SO$_2$—, —CO— or a C$_1$- to C$_{15}$-alkylene radical which may be substituted by alkyl, hydroxyl or halogen, or a cyclohexylidene radical which may be substituted by methyl up to 3 times.

2. Compounds according to claim 1, characterized in that, in the formula (II),

L represents

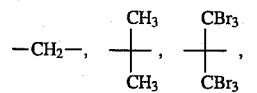

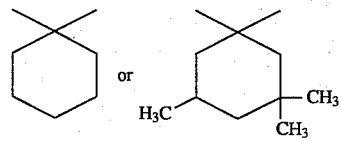

3. Compounds according to claim 1 from the group of compounds consisting of

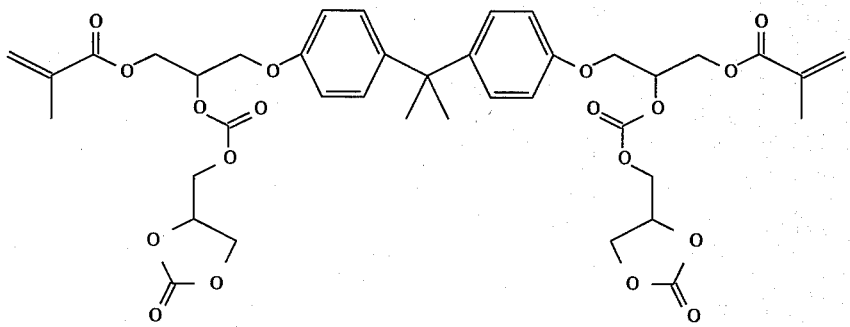

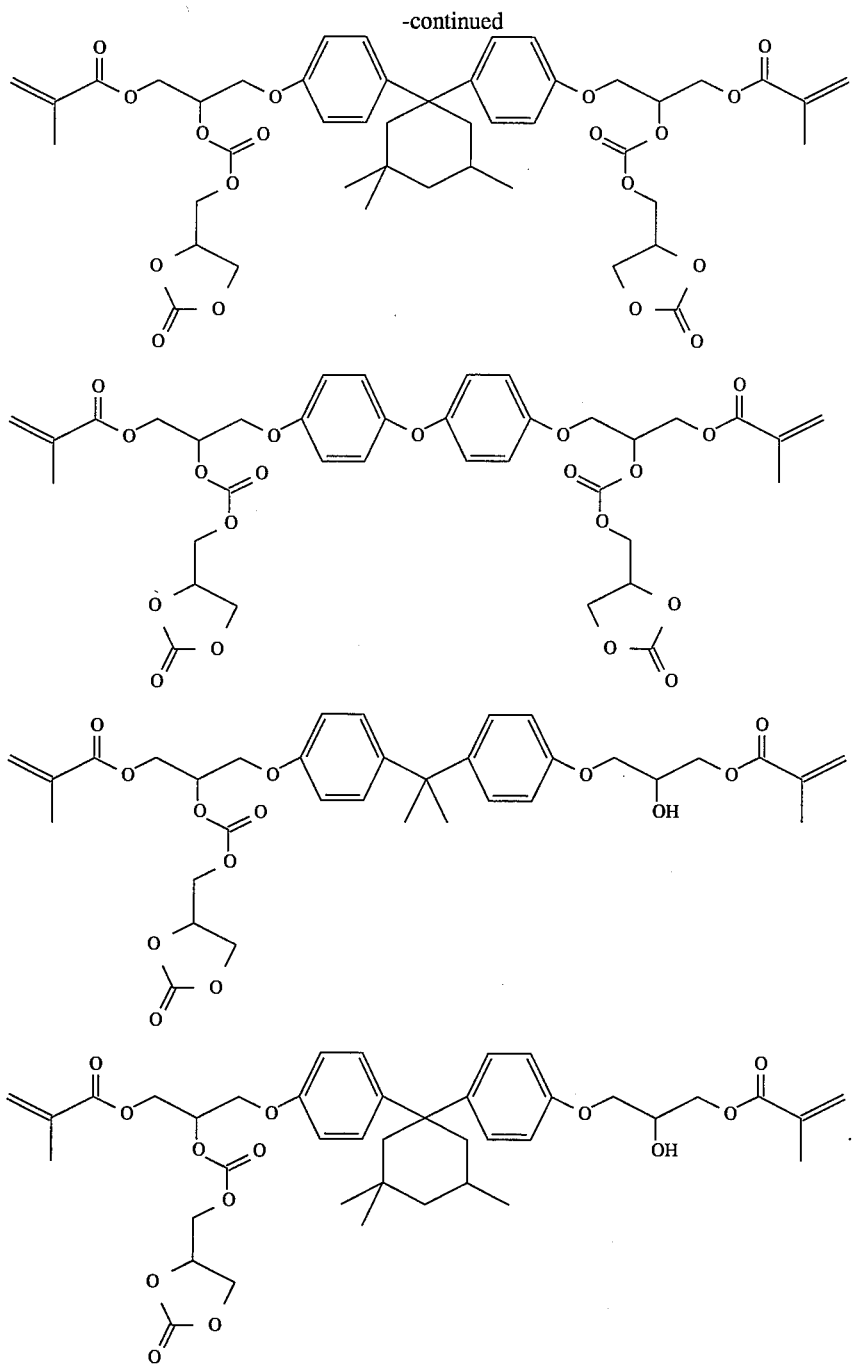
4. Process for the preparation of compounds of the formula (II)
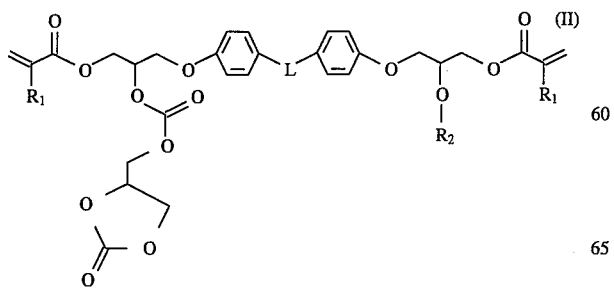
wherein
$R_1$ independently of one another represent hydrogen or methyl,
$R_2$ represents hydrogen or
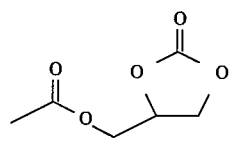
and
L represents a direct C—C bond, —O—, —S—, —SO$_2$—, —CO— or a $C_1$- to $C_{15}$-alkylene radical which may be substituted by alkyl, hydroxyl or halogen, or a cyclohexylidene radical which may be substituted by methyl up to 3 times
characterized in that compounds of the formula (IIa)

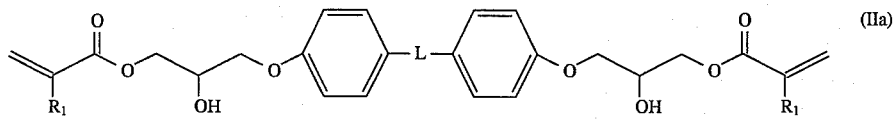

wherein
R₁ and L have the above-mentioned meaning,
are reacted with a chloroformic acid ester of the formula (III)

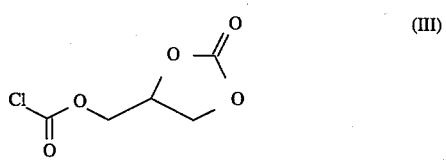

5. Process according to claim 4, characterized in that, in the formula (IIa)
L is

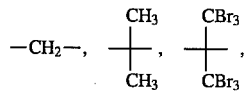

-continued

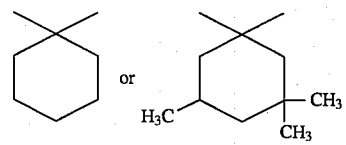

6. Restoration materials in dental technology, comprising compounds according to claims 1.

7. A dental restoration method, wherein, a composition comprising a compound of claim 1 is applied to a dental component.

* * * * *